(12) United States Patent
Mitsui

(10) Patent No.: US 6,926,406 B2
(45) Date of Patent: Aug. 9, 2005

(54) CONTACT LENS FOR CORRECTING MYOPIA AND/OR ASTIGMATISM

(76) Inventor: Iwane Mitsui, c/o Mitusi Medical Clinic if 3F Yamaguchi Kensetsu Second Bldg., 5-4-11 Akasaka, Minato-ku, Tokyo (JP)

( * ) Notice: Subject to any disclaimer, the term of this patent is extended or adjusted under 35 U.S.C. 154(b) by 109 days.

(21) Appl. No.: 10/712,944

(22) Filed: Nov. 13, 2003

(65) Prior Publication Data

US 2004/0070732 A1 Apr. 15, 2004

Related U.S. Application Data

(63) Continuation of application No. 10/073,081, filed on Feb. 12, 2002, now abandoned.

(30) Foreign Application Priority Data

Nov. 16, 2001 (JP) ........................................ 2001-351257

(51) Int. Cl.[7] ................................................. G02C 7/02
(52) U.S. Cl. ...................................................... 351/177
(58) Field of Search .............................. 351/160 R, 177

(56) References Cited

U.S. PATENT DOCUMENTS

| | | | | |
|---|---|---|---|---|
| 5,191,365 A | | 3/1993 | Stoyan | .................... 351/160 R |
| 5,428,412 A | | 6/1995 | Stoyan | ........................ 351/177 |
| 5,695,509 A | | 12/1997 | El Hage | ..................... 606/166 |
| 5,929,968 A | | 7/1999 | Cotie et al. | ............. 351/160 R |
| 5,963,297 A | | 10/1999 | Reim | ..................... 351/160 R |
| 6,582,077 B1 | * | 6/2003 | Tabb et al. | .................. 351/177 |

FOREIGN PATENT DOCUMENTS

| WO | WO 98/52090 | 11/1998 | ............ G02C/7/04 |
|---|---|---|---|
| WO | WO 02/41070 | 5/2002 | ............ G02C/7/04 |

* cited by examiner

Primary Examiner—Scott J. Sugarman
Assistant Examiner—Darryl J. Collins
(74) Attorney, Agent, or Firm—Renner, Kenner, Greive, Bobak, Taylor & Weber

(57) ABSTRACT

The present invention provides a myopia and/or astigmatism-correcting contact lens for correcting myopia and/or astigmatism based on the alteration in the shape of a patient's cornea. The myopia and/or astigmatism-correcting contact lens comprises a pressure zone having a first surface defined by the inner surface of the contact lens located on the side of the patient's cornea and positioned at the center of the contact lens. The first surface is formed in a concave shape having a curvature less than that of the central surface of the patient's cornea. The contact lens further includes a relief zone having a concave-shaped second surface defined by the inner surface of the contact lens located on the side of the patient's cornea and positioned at the periphery of the pressure zone, and an anchor zone having a concave-shaped third surface defined by the inner surface of the contact lens on the side of the patient's cornea and positioned at the periphery of the relief zone. The first surface has a curvature determined based on the shape of the patient's cornea to induce a specific desired alteration in the shape of the patient's cornea. Further, each of the curvatures of the first, second and third surfaces is arranged to satisfy the following formulas, $RC = BC + 7.0 \sim 9.0$ D (diopter), and $AC = BC + 2.0 \sim 4.0$ D where BC is the curvature of the first surface, RC is the curvature of the second surface, and AC is the curvature of the third surface.

6 Claims, 3 Drawing Sheets

CONTACT LENS FOR CORRECTING MYOPIA AND/OR ASTIGMATISM

CROSS-REFERENCE TO RELATED APPLICATION

This application is a continuation of U.S. patent application Ser. No. 10/073,081 filed Feb. 12, 2002 now abandoned.

FIELD OF THE INVENTION

The present invention relates to a contact lens for correcting myopia and/or astigmatism. More specifically, the present invention relates to a myopia and/or astigmatism-correcting contact lens for reshaping the cornea based upon corneal topography to effect correction of visual defects.

BACKGROUND OF THE INVENTION

Visual or optical defects which prevent parallel light rays entering the eye from focusing clearly on the retina exist in several varieties. In hyperopia (farsightedness), the point of focus lies behind the retina, generally because the axis of the eyeball is too short. In myopia (nearsightedness), the image is focused in front of the retina, generally because the axis of the eyeball is too long. In astigmatism, refraction is unequal on the different meridians of the eyeball, generally due to asymmetry in the shape of the eye.

Corrective glasses or contact lenses have been used to correct these defects, including convex (plus) lenses for hyperopia, concave (minus) lenses in myopia, and cylindrical lenses in astigmatism. More recently, a surgical technique, myopic or hyperopic keratomileusis has been used to alter cornea curvature and thereby improve refractive error. This method cuts and removes a predicted thickness of the corneal disk with a microkeratome. Additional surgical procedures such as radial keratotomy use microincisions in the cornea to surgically modify the curvature of the cornea and thereby reduce or eliminate myopia or astigmatism.

Photorefractive keratectomy (PRK) uses a laser to ablate the center of the cornea and thus change the cornea. In Automated Lamilar Keratectomy (ALK) pressure is placed on the cornea to bulge the central dome. A flap in the dome is then opened, layers of corneal tissue are removed and the flap is then closed. Procedures combining aspects of ALK/PRK are sometimes used, called LASIK (laser in situ keratectomy).

While these surgical procedures effect long lasting correction of visual defects, they present an inherent risk of permanent damage to a patient's eye. However slight this risk might be, many patients are unwilling to undergo these surgical procedures to correct the curvature of the cornea. Thus, there has existed a need to provide a non-surgical method for reshaping the cornea and thereby effecting correction of visual defects.

As one technique for satisfying such a demand, U.S. Pat. No. 5,695,509 provides an optical contact lens (contact lens) for non-surgically reshaping and altering the curvature of the cornea. When applied to the cornea of a patient, this optical contact lens (hereinafter, sometimes referred to as "contact lens") exerts a selective pressure on the cornea causing displacement of corneal tissue away from a pressure zone to a relief zone, thereby reshaping the patient's cornea and improving the patient's vision without surgical intervention. In general, the design of the optical contact lens induces change in the corneal topography of the patient's eye to make the cornea of a myopic eye more oblate.

This optical contact lens is tooled in response to the specific contour or topography of a patient's cornea and to affect a desired reshaping or correction of the eye's curvatures. When the contact lens is placed on the patient's cornea, a pressure zone of the contact lens exerts a relative selective pressure on the underlying or engaged region of the cornea to effect displacement of corneal tissue away from the region of pressure. A relief zone adjacent to the pressure zone does not contact the cornea and does not exert pressure on the cornea, but is an area where the contact lens is raised above the corneal surface. This area serves to receive corneal tissue which is displaced from the cornea underlying the pressure zone. An anchor zone adjacent to the relief zone and between the relief zone and the periphery of the contact lens controls or guides the reshaping of the corneal tissue, directing displaced tissue to the relief zone. The anchor zone also ensures good centration and maintenance of centration of the contact lens on the cornea thus providing predictability of the result and preventing overshooting the desired correction.

A contact lens of this invention useful in the treatment of myopia contains a central pressure zone, an adjacent annular relief zone, and an annular anchor zone adjacent to the relief zone and located between the relief zone and the periphery of the contact lens. When the contact lens is positioned on the patient's cornea, pressure is exerted by the central pressure zone on the approximate center of the corneal dome, thereby effecting displacement of corneal tissue away from the center of the dome and to the adjacent annular relief area. The pressure exerted at the anchor zone controls reformation of the corneal surface by guiding the displaced tissue into the relief zone. With time, the steep curvature of the myopic eye's corneal dome is flattened or reduced, and light incident over the central cornea will more correctly converge on the retina, thereby improving the patient's vision.

In order to effect the treatment of astigmatism for a patient's corneal dome having one or more curvatures, the contact lens' curvature is arranged in each of given axes to allow the pressure zone to be positioned so as to apply pressure at the steepest meridian, thereby reducing the steep meridian and minimizing or eliminating the difference in curvature. The characteristics of a contact lens for treating astigmatism are similar to those of a contact lens for correcting myopia.

The contact lens provided by the above U.S. Patent can be summarized as follows.

A myopia and/or astigmatism-correcting contact lens for correcting myopia and/or astigmatism based upon the alteration in the shape of a patient's cornea, comprising;

a pressure zone having a first surface defined by the inner surface of the contact lens located on the side of a patient's cornea and positioned at the center of the contact lens, wherein the first surface is formed in a concave shape having a curvature than that of the central surface of the patient's cornea;

a relief zone having a second surface defined by the inner surface of the contact lens located on the side of the patient's cornea and positioned at the periphery of the pressure zone, wherein the second surface is formed in a concave shape; and an anchor zone having a third surface defined by the inner surface of the contact lens located on the side of the patient's cornea and positioned at the periphery of the relief zone and, wherein the third surface is formed in a concave shape.

More specifically, in order to induce a specific desired alteration in the shape of the patient's cornea, the first surface has a curvature determined based on the shape of the patient's cornea, and each of the curvatures of the first, second and third surfaces is arranged to satisfy the following formulas, $RC=BC+3.00$ D (diopter), and $AC=BC+0.0-1.0$ D where BC is the curvature of the first surface, RC is the curvature of the second surface, and AC is the curvature of the third surface.

The contact lens having the RC and AC arranged as above could achieve some positive results. However, it was significantly effective only for European and American but less effective for Asian. Thus, the inventors have researched the shape of the cornea of Asian, particularly of Japanese, and have found out a desirable curvature of each of the aforementioned surfaces of the contact lens most effective for Asian, particularly for Japanese.

DISCLOSURE OF THE INVENTION

Based on this knowledge, it is an object of the present invention to provide a myopia and/or astigmatism-correcting contact lens having a curvature effective for Asian, particularly for Japanese.

According to the first aspect of the present invention, a myopia and/or astigmatism-correcting contact lens for correcting myopia and/or astigmatism based on the alteration in the shape of a patient's cornea, said myopia and/or astigmatism-correcting contact lens comprising;

a pressure zone having a first surface defined by the inner surface of said contact lens located on the side of the patient's cornea and positioned at the center of said contact lens, said first surface being formed in a concave shape having a curvature less than that of the central surface of the patient's cornea;

a relief zone having a second surface defined by the inner surface of said contact lens located on the side of the patient's cornea and positioned at the periphery of said pressure zone, said second surface being formed in a concave shape; and an anchor zone having a third surface defined by the inner surface of said contact lens on the side of the patient's cornea and positioned at the periphery of said relief zone, said third surface being formed in a concave shape, wherein said first surface has a curvature determined based on the shape of the patient's cornea to induce a specific desired alteration in the shape of the patient's cornea, and each of the curvatures of said first, second and third surfaces is arranged to satisfy the following formulas, $RC=BC+7.0-9.0$ D (diopter), and $AC=BC+2.0-4.0$ D where BC is the curvature of the first surface, RC is the curvature of the second surface, and AC is the curvature of the third surface.

It is preferred that, in the above myopia and/or astigmatism-correcting contact lens, each of the curvatures of said first, second and third surfaces is arranged to satisfy the following formulas, $RC=BC+7.5-8.5$ D, and $AC=BC+2.5-3.5$ D Alternatively, each of the curvatures of said first, second and third surfaces is preferably arranged to satisfy the following formulas, $RC=BC+$about 8.0 D, and $AC=BC+$about 3.0 D The myopia and/or astigmatism-correcting preferably has a diameter ranging from about 9.0 to about 11.0 mm, and more preferable, about 9.5 to about 10.5 mm, and especially preferable, about 10 mm.

According to the second aspect of the present invention, a myopia and/or astigmatism-correcting contact lens for correcting myopia and/or astigmatism based on the alteration in the shape of a patient's cornea, said myopia and/or astigmatism-correcting contact lens comprising;

a pressure zone having a first surface defined by the inner surface of said contact lens located on the side of a patient's cornea and positioned at the center of said contact lens, said first surface being formed in a concave shape having a curvature less than that of the central surface of the patient's cornea;

a relief zone having a second surface defined by the inner surface of said contact lens located on the side of the patient's cornea and positioned at the periphery of said pressure zone, said second surface being formed in a concave shape;

a first anchor zone having a third surface defined by the inner surface of said contact lens on the side of the patient's cornea and positioned at the periphery of said relief zone, said third surface being formed in a concave shape; and a second anchor zone having a fourth surface defined by the inner surface of said contact lens on the side of the patient's cornea and positioned at the periphery of said first anchor zone, said fourth surface being formed in a concave shape, wherein said first surface has a curvature determined based on the shape of the patient's cornea to induce a specific desired alteration in the shape of the patient's cornea, and each of the curvatures of said first, second, third and fourth surfaces is arranged to satisfy the following formulas, $RC=BC+11.00-13.0$ D $AC1=BC+3.0-5.0$ D, and $AC2=BC+4.0-6.0$ D where BC is the curvature of the first surface, RC is the curvature of the second surface, AC 1 is the curvature of the third surface, and AC 2 is the curvature of the fourth surface.

It is preferred that, in the above myopia and/or astigmatism-correcting contact lens, each of the curvatures of said first, second, third and fourth surfaces is arranged to satisfy the following formulas, $RC=BC+11.5-12.5$ D, $AC1=BC+3.5-4.5$ D and $AC2=BC+4.5-5.5$ D Alternatively, each of the curvatures of said first, second, third and fourth surfaces is preferably arranged to satisfy the following formulas, $RC=BC$+about 12 D, $AC1=BC$+about 4 D, and $AC2=BC$+about 5 D According to the third aspect to the present invention, a myopia and/or astigmatism-correcting contact lens for correcting myopia and/or astigmatism based on the alteration in the shape of a patient's cornea, said myopia and/or astigmatism-correcting contact lens comprising;

a pressure zone having a first surface defined by the inner surface of said contact lens located on the side of a patient's cornea and positioned at the center of said contact lens, said first surface being formed in a concave shape having a curvature less than that of the central surface of the patient's cornea;

a relief zone having a second surface defined by the inner surface of said contact lens located on the side of the patient's cornea and positioned at the periphery of said pressure zone, said second surface being formed in a concave shape;

a first anchor zone having a third surface defined by the inner surface of said contact lens on the side of the patient's cornea and positioned at the periphery of said relief zone, said third surface being formed in a concave shape; and a second anchor zone having a fourth surface defined by the inner surface of said contact lens on the side of the patient's cornea and positioned at the periphery of said first anchor zone, said fourth surface being formed in a concave shape, wherein said first surface has a curvature determined based on the shape of the patient's cornea to induce a specific desired alteration in the shape of the patient's cornea, and each of the curvatures of said first, second, third and fourth surfaces is arranged to satisfy the following formulas, $RC=BC$+12.5–14.5 D, $AC1=BC$+3.0–5.0 D, and $AC2=BC$+4.0–6.0 D where BC is the curvature of the first surface, RC is the curvature of the second surface, AC 1 is the curvature of the third surface, and AC 2 is the curvature of the fourth surface.

It is preferred that in the above myopia and/or astigmatism-correcting contact lens as defined in claim 10, wherein each of the curvatures of said first, second, third and fourth surfaces is arranged to satisfy the following formulas, $RC=BC$+13.0–14.0 D, $AC1=BC$+3.5–4.5 D, and $AC2=BC$+4.5–5.5 D Alternatively, each of the curvatures of said first, second, third and fourth surfaces is preferably arranged to satisfy the following formulas, $RC=BC$+about 13.5 D, $AC\ 1=BC$+about 4 D, and $AC2=BC$+about 5 D, The myopia and/or astigmatism-correcting contact lens may have a diameter ranging from about 9.6 to about 11.6 mm, preferable about 10.1 to about 11.6 mm, more preferable, about 10.6 to about 11.2 mm, and especially preferable, about 10.2, 10.4, 10.6, 10.8, and 11.0 mm.

As with the optical contact lens of the aforementioned U.S. Patent, in a myopia and/or astigmatism-correcting contact lens of the present invention, application of this contact lens to a patient's cornea results in reshaping of the cornea and provides improved visual acuity. In a preferred embodiment, once a patient's cornea has achieved an optimal shape, as determined by functional visual acuity, the contact lens of the present invention may be temporarily removed without loss of visual correction. However, a patient may maintain the desired shape of the cornea by wearing the optical contact lens for a short period of time, e.g., approximately three to eight hours per day. For example, in some instances, a patient may wear the contact lens one or two nights a week or every night during sleep to maintain the desired shape and functional vision.

BEST MODE FOR CARRYING OUT THE INVENTION

Figure 1:
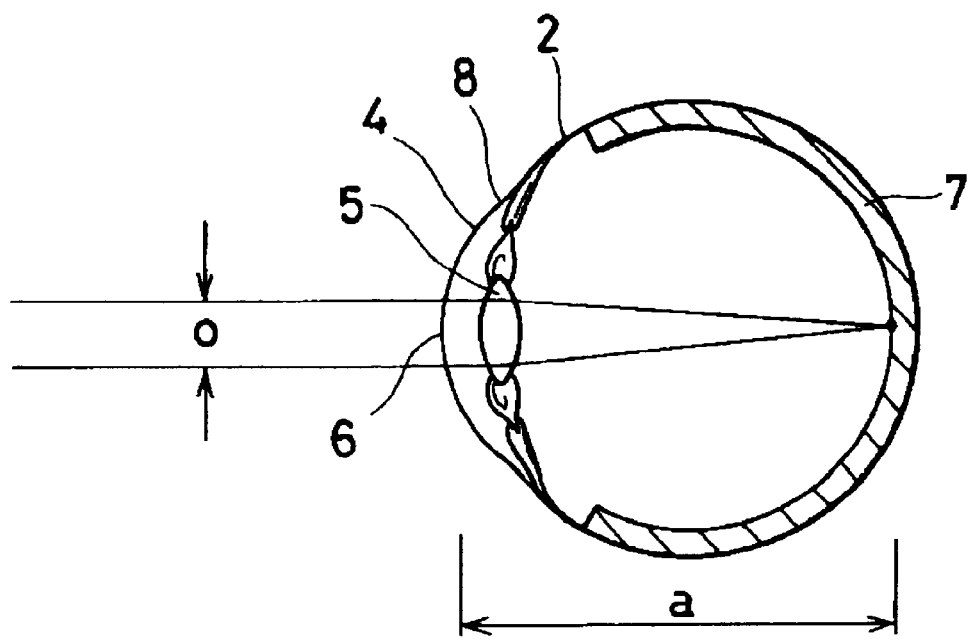
FIG. 1 is a schematic side sectional view of an average normal eye.
Figure 2:
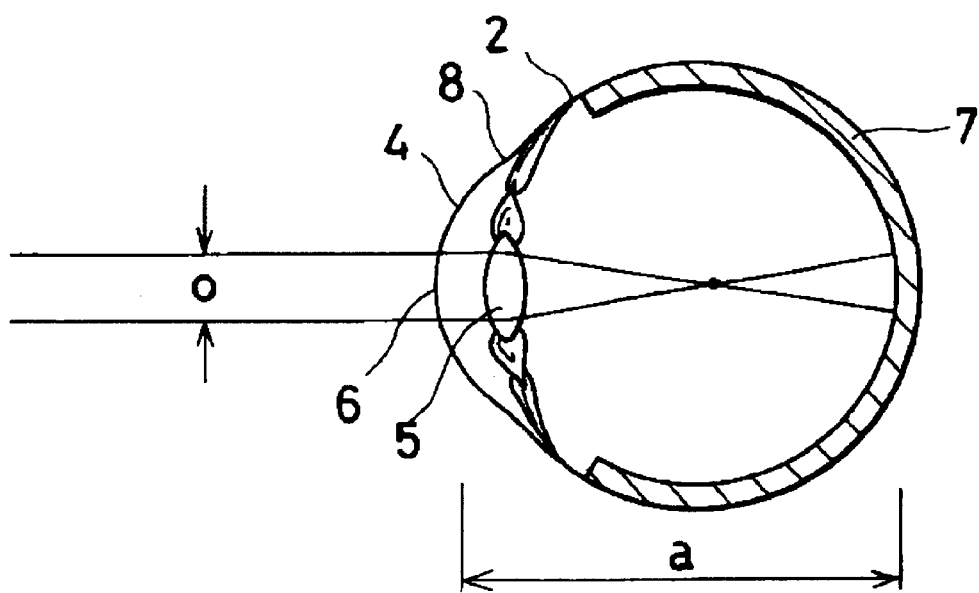
FIG. 2 is a schematic sectional view of a myopic eye.
Figure 3:
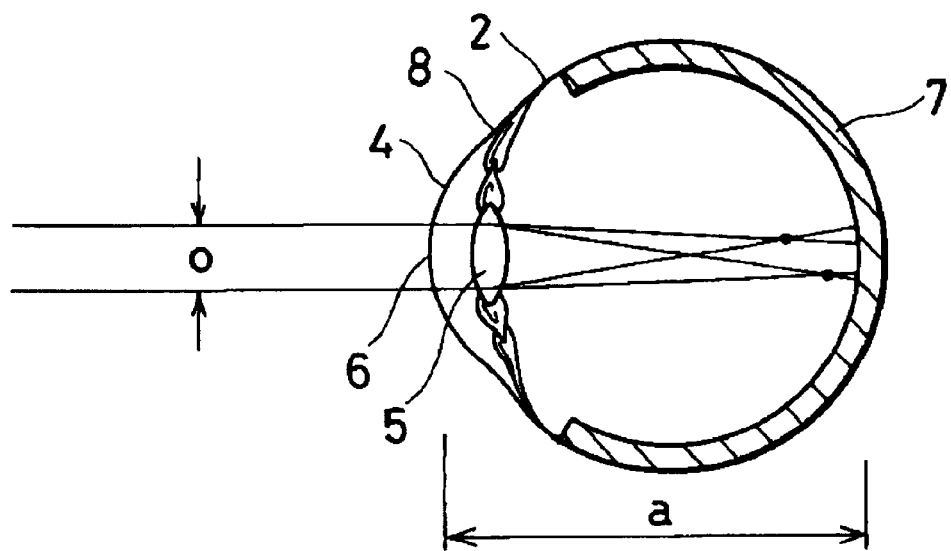
FIG. 3 is a schematic sectional view of an astigmatic eye.

In order to help understanding of a myopia and/or astigmatism-correcting contact lens according to a preferred embodiment of the invention, the general state of eyes will be first described with referred to FIGS. 1 to 3.

FIG. 1 shows a normal eye containing a normal cornea 2. The portion of the cornea 2 which projects over the lens 5 is termed the corneal dome 4. The corneal dome 4 is generally considered rotationally symmetrical and aspherical in shape, with the approximate dome center 6 having essentially the highest projection away from the center of the eye. A generally circular optical zone o transmits incident light which normally converges on the retina 7.

Defects in visual acuity are correlated with distortions in the shape of the cornea. As shown in FIG. 2, convergence occurs in front of the retina in a myopic eye (nearsighted), and is associated with an elongated axis a and a steepened or heightened corneal dome 4. In an eye having astigmatism, multiple curvatures of the cornea cause multiple areas of convergence as shown in FIG. 3.

The degree of corneal distortion and precise location and size of a patient's corneal dome center 6 and dome periphery 8 may be determined by one of skill in the art using a videokeratoscope or corneal topographer. As described in pending U.S. application Ser. No. 08/046,619, measurements of the contour of the cornea of the human eye have been used to facilitate the design and fit of contact lenses, as well as for use and performance of surgical procedures.

In a conventional videokeratoscope used to measure the cornea, concentric rings of light from a source of light within a housing are directed onto a cornea and reflected by the cornea onto the film of a camera as an image of the rings. The deviation of the rings from their known concentricity is measured and this data is processed mathematically to determine the actual contour of the cornea, which is not a perfect sphere and which differs from one individual to another. Conventional photokeroscopes are disclosed, for example, in U.S. Pat. Nos. 3,248,162 and 3,598,478. Videokeratoscopes or corneal topographers are disclosed for example, in U.S. Pat. Nos. 4,978,213, 5,227,818 and U.S. patent application Ser. No. 08/046,619. In general, a corneal topographer includes a camera means, such as a charged coupled device camera system for sensing the images of rings of light reflected from the cornea. The camera apparatus sends standard video signals to a computer, such as a conventional, commercially available image processor, which digitize the video signals. The computer analyzes the digital data and produces data useful in determining the contour of the cornea of the human eye. A corneal topographer apparatus which automatically centers and focuses the corneal image reflected from a patient's cornea onto a charge coupled device camera system is disclosed in U.S. patent application Ser. No. 08/046,619.

Any of the above-described methods, as well as others known to those of skill in the art, may be used to determine the topography of the cornea of a patient to be fitted with a contact lens of the present invention. Whatever method is utilized, the data is analyzed to determine the corneal condition, e.g., regular, irregular, or astigmatism by methods generally known in the art. The location and curvature of the corneal dome 4 and center 6 is determined. Using these measurements, as well as the degree of refractive error to be corrected, a contact lens or a lens of the present invention is machined to apply selective pressure to areas of the patient's cornea in order to effect a desired displacement and reshaping of the cornea. Reformation or reshaping of the patient's cornea results in improvement of the patient's vision.

Figure 4:
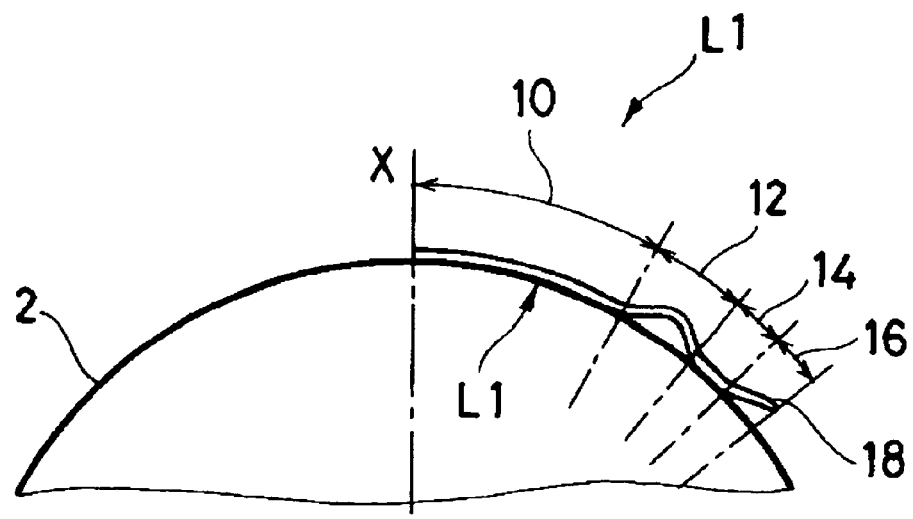
FIG. 4 is a schematic sectional view of a contact lens according to a first embodiment of the present invention suitable for treating the myopic eye of FIG. 2.

The contour and shape of the contact lens L1 according to a first embodiment are shown in FIG. 4 in an exaggerated form. The contour of the contact lens L1 is designed to treat myopia or astigmatism. In FIG. 4, the contact lens L1 is symmetrical with respect to the axis X.

The contact lens L1 includes at its center a pressure zone 10 which will overlay or engage a region of the corneal surface where alteration is desired. When the contact lens L1 is placed on the eye, the pressure zone 10 will apply a relative pressure to the underlying or engaged region of the cornea. It is understood that the contact lens L1 is separated from the cornea by fluid, e.g., tears present between the lens and the surface of the cornea but the fluid follows the contour of the cornea.

The contact lens L1 also includes an annular relief zone 12 positioned at the periphery of the pressure zone 10. The relief zone 12 is an area adjacent to the pressure zone 10 that creates a space or void between the surface of cornea and the contact lens. No pressure is applied from the relief zone 12 onto the underlying region of the cornea. In contrast to the pressure zone 10, the area between the relief zone 12 and the underlying corneal surface is sufficiently spacious to receive corneal tissue displaced by pressure applied at the pressure zone 10. An annular anchor zone 14 is located adjacent to the periphery of the relief zone 12. The anchor zone 14 is in contact with the cornea and exerts minimal pressure on the cornea for purposes of anchoring the contact lens on the corneal surface to achieve and maintain good centration or positioning. By applying relative pressure adjacent to the relief zone 12, the anchor zone 14 guides the displaced corneal tissue into the area under the relief zone 12.

The position of the pressure zone 10 on the cornea is important to the contact lens's function of providing useful reshaping of the cornea. Referring to FIG. 4, in a contact lens designed to treat myopia, the pressure zone 10 is positioned to apply pressure at the approximate center of the corneal dome. The anchor zone 14 maintains the contact lens's position on the cornea and controls the direction of corneal tissue displacement into the relief zone.

Preferably, the contact lens L1 of the present invention includes a second annular relief zone 16 at the periphery 18 of the contact lens. The second relief zone 16 is raised away from the cornea 2, e.g., to approximately 80–100 μm at the periphery 18 of the contact lens, to assist in the movement of fluid and nutrients under the contact lens, and also to permit easy removal of the contact lens from the eye.

The specific location and size of the pressure zone, relief zone, anchor zone, and second relief zone will differ with the specific condition of the patient's eye and corneal topography, and with the type of correction desired.

As shown in FIG. 4, when the contact lens is applied to an eye, the pressure zone 10 engages the underlying corneal tissue. The term "Engages" means that portion of the contact lens is separated from the corneal tissue essentially only by tear fluid, and the "engagement" causes pressure to be exerted by the pressure zone 10 of the contact lens onto the underlying corneal tissue. The pressure applied at the pressure zone 10 causes the underlying cornea to be displaced away from the pressure zone.

The relief zone 12 is that portion of the contact lens which, when positioned on an eye, does not "engage" the underlying cornea, but in contrast, is recessed or raised away from the cornea, creating an annular space or zone between the contact lens and the corneal surface for receiving displaced corneal tissue.

When the contact lens is applied to an eye, the annular anchor zone 14 engages the underlying cornea. The anchor zone 14 exerts a minimal pressure on the corneal surface underlying the contact lens at a location adjacent to the relief zone 12 and between the relief zone 12 and the periphery 18. The pressure exerted by the anchor zone 14 cooperates with the central pressure zone 10 and guides displaced corneal tissue into the space underlying the contact lens at the relief zone 12. Pressure exerted by the anchor zone 14 also stabilizes the contact lens on the corneal surface and permits achievement and maintenance of good centration of the contact lens on the cornea. Like the relief zone 12, a second relief zone 16 does not engage the underlying cornea. The second relief zone 16 facilitates easy access of fluid and nutrients under the contact lens and also permits easy "lift off" or removal of the contact lens from the corneal surface. In general, the periphery 18 of the contact lens has a sufficient curvature to be raised away from the cornea for access of fluids, e.g., approximately 80–100 μm, and preferably about 90–100 μm.

The design of a contact lens to correct astigmatism of the eye as shown in FIG. 3 is in general similar to the contact lens of FIG. 4 for treating a myopic eye.

The concave surface of the contact lens of the present invention is formed with a continuous aspheric curvature from center to periphery, that is with a gradual change of curvature into each specified zone. The continuous curve is achieved by machining the contact lens in accordance with a mathematical analysis of the best curve fit for the desired distances between the surface of the cornea at each of the specified zones and the contact lens.

The contact lens of the present invention may be fabricated from materials and using methods known to be useful, for example, in the manufacture of conventional contact lenses. Such materials include those useful in fabricating conventional gas (oxygen) permeable contact lenses, e.g., fluroperm (Paragon Optical Co.) or any oxygenated rigid plastic available and known to be useful in fabrication of conventional contact lenses. An especially preferred lens material is fluroperm 60 or 90, because it has high DK value (oxygen transmissibility). In a preferred embodiment, the contact lenses will also have optical properties to correct refractive error during the reshaping of the cornea.

The contact lenses of the present invention are machined to provide the appropriate reshaping of a particular patient's eye. The eye's corneal topography is defined and mapped using conventional corneal topography equipment as described above. The refraction of the eye is measured by conventional techniques. A diagnosis of the condition to be treated is made, e.g., myopia or astigmatism, and the amount of refractive error is determined. The patient's corneal topography is analyzed to select the appropriate parameters for the patient's contact lens, including the position, size and location of the corneal dome, the shape factor (e.g., deviation from a perfect sphere), and curvatures of the contact lens to match the patient's topography.

Measurements of a patient's corneal topography are adjusted for the desired correction and used to specify the dimensions of the corrective contact lens. For the myopic eye shown in FIG. 2, the approximate size of the optical zone o, or heightened area of the corneal dome is measured as the radius (or diameter) from the approximate center of the dome 6 to the approximate mid-periphery 8. Generally, for a contact lens having a total diameter of about 10 mm, the diameter of the optical zone will vary from about 4 to about 7.5 mm. An area within the patient's optical zone o is analyzed to determine the average diopter of the optical zone, which determines the base diopter of the corrective contact lens. As shown in FIG. 4, the relative size and position, e.g., annular diameters of the pressure zone 10 and the diopter and annular diameter of the relief zone 12 is determined in part by the correction needed and the degree of the desired therapy.

The desired diopter of the pressure zone 10 is calculated to apply a relative pressure to the underlying cornea according to the diopter of cornea to be corrected, and is generally calculated by subtracting a given value from the diopter of the cornea to be corrected, in which the given value is preferable to be 1.5–4.5, particularly about 3.

The factors disclosed in the aforementioned U.S. patent may be used as factors in addition to those described above and bellow.

The rate of curvedness (curvature) RC of the curve of the annular relief zone 12 (the second surface) is machined to satisfy the following formula, $RC = BC + 7.0 - 9.0$ D $= BC + 7.5 - 8.5$ D (preferably)

$= BC + $ about $8.0$ D (more preferably)

where BC is the curvature of the curved surface of the aforementioned pressure zone (the first surface).

The rate of curvedness (curvature) RC of the curve of the anchor zone 14 (the third surface) is machined to satisfy the following formula, $RC = BC + 2.0 - 4.0$ D $= BC + 2.5 - 3.5$ D (preferably)

$= BC + $ about $3.0$ D (more preferably)

where BC is the curvature of the curved surface of the aforementioned pressure zone (the first surface).

Then, the contact lens is machined to provide a continuous curvature from the annular anchor zone 14 through the second relief zone 16 to the raised periphery 18 of the contact lens. The periphery 18 of the contact lens is machined to be raised approximately 80–100 μm from the surface of the cornea to provide edge lift.

The general diameter of the contact lens of the first embodiment is arranged in the range of about 9.0 to about 11.0 mm (4.5 to 5.5 mm in radius), preferably about 9.5 to about 10.5 mm (4.75 to 5.25 mm in radius), and most preferably about 10 mm (about 5 mm in radius).

The diameter of the central pressure zone 10 is arranged in the range of about 4 to 7.5 mm (2 to 3.75 mm in radius), preferably 4.5 to 7.0 mm (2.25 to 3.5 mm in radius), and most preferably 5.8 to 6.5 mm (2.9 to 3.25 mm in radius). The annular radius of the relief zone is arranged preferably in the range of 0.5 to 1.0 mm, particularly at about 0.7 mm. The annular radius of the anchor zone is arranged preferably in the range of about 0.6 to about 0.8 mm. The annular radius of the second relief zone is arranged preferably in the range of 0.3 to 0.6 mm.

The method of forming a contact lens for the treatment of astigmatism is similar to that for forming a contact lens to treat a myopic eye. The general diameter and average curvature of the optical zone is determined. Next, the curvature of the pressure and relief zones are calculated, as well as the anchor zone and second relief zone curvatures.

The specific curvature of each contact lens is determined from the topography of the eye and the desired level of visual correction needed. One general method for calculating the curvatures of a contact lens for treating a myopic eye is described below. It is understood that several methods may be used to achieve a contact lens of the present invention. Thus, the following description is meant to be exemplary, and does not limit the invention.

First, the patient's corneal topography is measured. Examining a central portion of the cornea, e.g., the optical zone at about 4–5 mm in central diameter (about 2–2.5 mm in central radius), an average diopter is determined.

After determining the average diopter of the center portion of the cornea, a desired diopter is arranged based on the determined average diopter to provide a diopter of the pressure zone 10 of the contact lens L1.

Each curvature of the relief zone and anchor zone of the contact lens to treat myopia is determined using the aforementioned formula.

The other factors may be determined by those described in the aforementioned U.S. patent.

After the patient has worn a contact lens of the present invention for a period of time, the patient is examined to record progress in reaching an optimal shape or optimal level of correction. For example, the patient may be examined approximately weekly or monthly by measuring corneal topography and comparing new measurements of corneal shape and visual acuity with prior records. An optimal shape of the cornea is that shape which permits good correction of the patient's visual defect to obtain functional vision, e.g., that vision acceptable to the patient without contact lenses.

For a very myopic patient, a plurality of contact lenses having different correction diopters may be prepared to allow the contact lens to be changeably worn depending on the progress in correction.

Examples of such contact lenses will be described bellow.

A contact lens L2 according to a second embodiment comprises: a pressure zone 110 having a first surface defined by the inner surface of the contact lens located on the side of a patient's cornea and positioned at the center of the contact lens, wherein the first surface is formed in a concave shape having a curvature less than that of the central surface of the patient's cornea; a relief zone 112 having a second surface defined by the inner surface of the contact lens located on the side of the patient's cornea and positioned at the periphery of the pressure zone 111, wherein the second surface is formed in a concave shape; a first anchor zone 114a having a third surface defined by the inner surface of the contact lens on the side of the patient's cornea and positioned at the periphery of the relief zone 112, wherein the third surface is formed in a concave shape; and a second anchor zone 114b having a fourth surface defined by the inner surface of the contact lens on the side of the patient's cornea and positioned at the periphery of the first anchor zone 114a, wherein the fourth surface is formed in a concave shape.

The contact lens L2 has the curved surfaces arranged to satisfy the following formulas, $$RC=BC+11.00-13.0\ D$$

$$AC\ 1=BC+3.0-5.0\ D,\ \text{and}$$

$$AC\ 2=BC+4.0-6.0\ D$$

where BC is the curvature of the first surface, RC is the curvature of the second surface, AC 1 is the curvature of the third surface, and AC 2 is the curvature of the fourth surface.

Preferably, the above relationship is arranged as follows, $$RC=BC+11.5-12.5\ D,$$

$$AC\ 1=BC+3.5-4.5\ D,\ \text{and}$$

$$AC\ 2=BC+4.5-5.5\ D$$

and, most preferably, the above relationship is arranged as follows.

$$RC=BC+\text{about}\ 12\ D,$$

$$AC\ 1=BC+\text{about}\ 4\ D,$$

$$AC\ 2=BC+\text{about}\ 5\ D$$

A contact lens L3 according to a third embodiment comprises a pressure zone, a relief zone, a first anchor zone and a second anchor zone as with the contact lens L2 of the second embodiment. However, these are different in the relationship between respective curvatures of the surfaces as follows.

The contact lens L3 has the curved surfaces arranged to satisfy the following formulas, $$RC=BC+12.5-14.5\ D$$

$$AC\ 1=BC+3.0-5.0\ D,\ \text{and}$$

$$AC\ 2=BC+4.0-6.0\ D$$

where BC is the curvature of the first surface, RC is the curvature of the second surface, AC 1 is the curvature of the third surface, and AC 2 is the curvature of the fourth surface.

Preferably, the above relationship is arranged as follows, $$RC=BC+13.0-14.0\ D,$$

$$AC\ 1=BC+3.5-4.5\ D,\ \text{and}$$

$$AC\ 2=BC+4.5-5.5\ D,$$

and, more preferably, the above relationship is arranged as follows.

$$RC=BC+\text{about}\ 13.5\ D,$$

$$AC\ 1=BC+\text{about}\ 4\ D,\ \text{and}$$

$$AC\ 2=BC+\text{about}\ 5\ D$$

The diameters of the contact lens L2 and L3 are approximately the same and arranged preferably in the range of about 9.6 to about 11.6 mm, more preferably about 10.1 to about 11.3 mm, further 10.6 to 11.2 mm, and are specifically arranged at either one of about 10.2, 10.4, 10.6, 10.8, and 11.0 mm.

The diameter of the central pressure zone 110 is arranged in the range of about 4 to about 7.5 mm (2 to 3.75 mm in radius), preferably 4.5 to 7.0 mm (2.25 to 3.5 mm in radius), more preferably 5.8 to 6.5 mm (2.9 to 3.25 mm in radius). The annular radius of the relief zone 112 is arranged preferably in the range of 0.5 to 1.0 mm, particularly at about 0.7 mm. The annular radius of the first anchor zone 114a is arranged preferably in the range of about 0.5 to about 0.9 mm, particularly at about 0.6 mm. The annular radius of the second anchor zone 114b is arranged preferably in the range of about 0.4 to about 0.9 mm, particularly at about 0.6 mm. The second relief zone 116 is provided at the outer periphery of the second anchor zone 114b, and an annular radius of the second anchor zone 114b is arranged preferably in the range of about 0.3 to about 0.6 mm, particularly at about 0.4 mm.

The following examples will be referred to help better understanding of the invention.

EXAMPLES

Example 1 m With the Features of the Contact Lens L1 of the First Embodiment

A Japanese patient A initially wore a soft contact lens every day to correct myopia. The patient was diagnosed with myopia through the measurement of refractive error. According to the measurement of the topography of central curves of the right and left eyes, the diopter of the right eye was 38.50 (refractive error: −4.25, uncorrected vision: 0.1) and the diopter of the left eye was 39.00 (refractive error: −4.00, uncorrected vision: 0.1).

Based on the above measurements, BCs of the contact lenses of the patient's right and left eyes were arranged at 35.50 D and 36.00 D, respectively.

Then, according to the present invention, RC and AC were determined using the following two formulas.

$$RC=BC+8.0\ D$$

$$AC=BC+3.0\ D$$

As a result, RC and AC of the right eye's contact lens were 43.50 D and 38.50 D, respectively. Further, RC and AC of the left eye's contact lens were 44.0 D and 39.00 D, respectively.

Then, the general diameter of the contact lens was arranged at 10 mm, the diameter of the central pressure zone 10 being arranged at 6.0 mm (3.00 mm in radius), the annular radius of the relief zone 12 being arranged at 0.7 mm, the annular radius of the anchor zone 14 being arranged at 0.7 mm, and the annular radius of the second relief zone being arranged at 0.6 mm.

By using the above parameters, the contact lens L1 having the configuration of the example 1 shown in FIG. 4 was fabricated.

On the other hand, RC and AC were determined using the following two formulas which have heretofore been used in U.S. as described above.

$$RC = BC + 3.0 \text{ D}$$

$$AC = BC + 0.0 \text{ D}$$

As a result, RC and AC of the right eye's contact lens were 38.50 D and 35.50 D, respectively. RC and AC of the left eye's contact lens were 39.00 D and 36.00 D, respectively.

Then, using the same diameters as those of the inventive example, a contact lens as a comparative example was fabricated.

The contact lenses of the inventive example and the comparative example were worn by the patient A, and their results were compared with each other.

More specifically, the contact lenses as the comparative example were first worn by the myopic patient A at bedtime of night for one week. As a result, the right and left eyes of the patient A had 37.75 diopter (refractive error: −3.50, uncorrected vision: 0.2) and 38.00 diopter (refractive error: −3.25, uncorrected vision: 0.3), respectively, and some improvement was observed. However, once quitting the wearing, the original state was brought back in a week.

After that, the contact lenses according to the example 1 of the invention were worn by the patient A in the same way as that of the comparative example. As a result, the right and left eyes of the patient A had 37.00 diopter (refractive error: −1.75, uncorrected vision: 0.9) and 37.00 diopter (refractive error: −1.50, uncorrected vision: 1.0), respectively, and significant improvement was observed. Then, after the patient A continued the wearing under the above condition for a month, the effect was measured. As a result, the right and left eyes of the patient A had 36.25 diopter (refractive error: −0.25, uncorrected vision: 1.5) and 36.00 diopter (refractive error: −0.25, uncorrected vision: 1.5), respectively. Thus, the effect has been apparently proved.

Examples 2 and 3 m With the Features of the Contact Lenses L2 and L3 of the Second and Third Embodiments A Japanese patient B initially wore a soft contact lens every day to correct myopia. The patient was diagnosed with myopia through the measurement of refractive error. According to the measurement of the topography of central curves of the right and left eyes, the diopter of the right eye was 41.25 (refractive error: −6.25, uncorrected vision: 0.01) and the diopter of the left eye was 41.50 (refractive error: −6.50, uncorrected vision: 0.01).

Based on the above measurements, BCs of the contact lenses of the patient's right and left eyes were arranged at 38.25 D and 38.50 D, respectively.

Then, according to the present invention, RC, AC 1 and AC 2 were determined using the following three formulas.

$$RC = BC + 12.0 \text{ D}$$

$$AC\ 1 = BC + 5.0 \text{ D}$$

$$AC\ 2 = BC + 4.0 \text{ D}$$

As a result, RC, AC 1 and AC 2 of the right eye's contact lens of the example 2 were 50.25 D, 43.25 D and 42.25 D, respectively. Further, RC, AC 1 and AC 2 of the left eye's contact lens were 50.50 D, 43.50 D and 42.50 D, respectively.

Then, for the contact lens of the example 3, RC, AC 1 and AC 2 were determined using the following three formulas.

$$RC = BC + 13.5 \text{ D}$$

$$AC\ 1 = BC + 5.0 \text{ D}$$

$$AC\ 2 = BC + 4.0 \text{ D}$$

As a result, RC, AC 1 and AC 2 of the right eye's contact lens of the example 3 were 51.75 D, 43.25 D and 42.25 D, respectively. Further, RC, AC 1 and AC 2 of the left eye's contact lens were 52.00 D, 43.50 D and 42.50 D, respectively.

Then, the general diameter of the contact lenses according to the example 2 and 3 was arranged at 10 mm, the diameter of the central pressure zone 10 being arranged at 6.0 mm (3.00 mm in radius), the annular radius of the relief zone 12 being arranged at 0.7 mm, the annular radius of the first anchor zone 14 being arranged at 0.6 mm, the annular radius of the second anchor zone being arranged at 0.6 mm, and the annular radius of the second relief zone being arranged at 0.4 mm.

Figure 5:
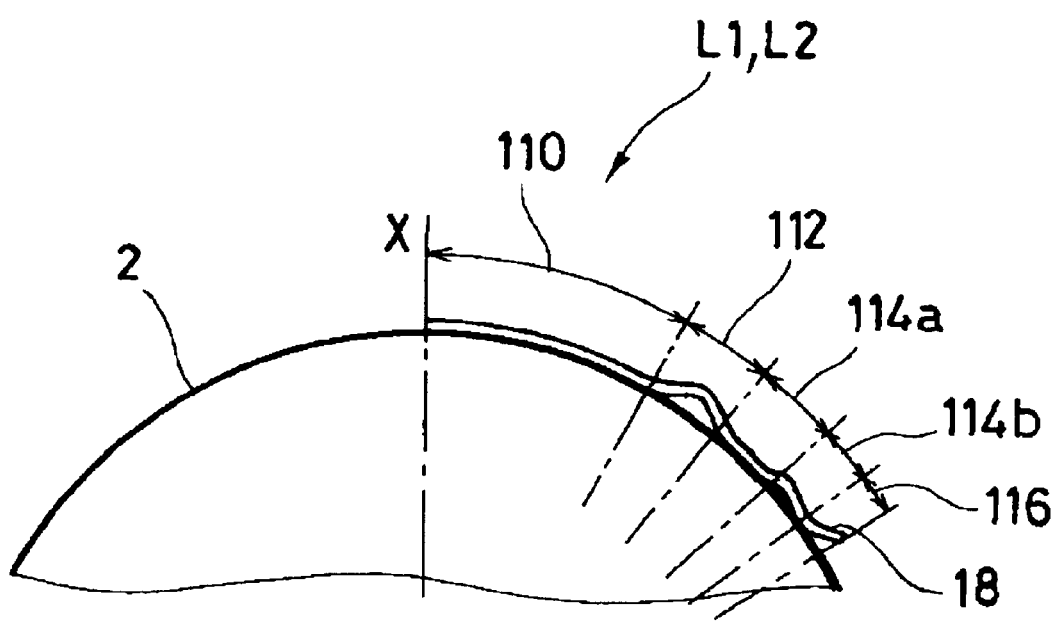
FIG. 5 is a schematic sectional view of a contact lens according to second and third embodiments of the present invention suitable for treating the myopic eye of FIG. 2.

By using the above parameters, the contact lenses L2 and L3 having the configurations of the examples 2 and 3 shown in FIG. 5 were fabricated.

On the other hand, RC and AC were determined using the following two formulas which have heretofore been used in U.S. as described above.

$$RC = BC + 3.0 \text{ D}$$

$$AC = BC + 0.0 \text{ D}$$

As a result, RC and AC of the right eye's contact lens were 41.25 D and 38.25 D, respectively. RC and AC of the left eye's contact lens were 41.50 D and 38.50 D, respectively.

Then, using the same diameters as those of the example 1, a contact lens as a comparative example 2 was fabricated.

The contact lenses of the examples 2 and 3 and the comparative example 2 were worn by the patient B, and their results were compared with each other.

More specifically, the contact lenses of the comparative example 2 were worn by the patient B at bedtime of night for one week. As a result, the right and left eyes of the patient B had 40.75 diopter (refractive error: −5.50, uncorrected vision: 0.08) and 40.50 diopter (refractive error: −5.75, uncorrected vision: 0.07), respectively, and some improvement was observed. However, once quitting the wearing, the original state was brought back in a week.

After that, the contact lenses according to the example 2 of the invention were worn by the patient B in the same way as that of the comparative example. As a result, the right and left eyes of the patient B had 39.75 diopter (refractive error: −4.25, uncorrected vision: 0.2) and 39.50 diopter (refractive error: −4.00, uncorrected vision: 0.3), respectively, and significant improvement was observed. Then, after the patient B continued the wearing under the above condition for a month, the effect was measured. As a result, the right and left eyes of the patient B had 39.25 diopter (refractive error: −2.50, uncorrected vision: 0.7) and 39.00 diopter (refractive error: −2.25, uncorrected vision: 0.8), respectively.

After that, the contact lenses according to the example 3 of the invention were successively worn by the patient B in the same way as that of the example 2. As a result, the right and left eyes of the patient B had 38.25 diopter (refractive error: −0.50, uncorrected vision: 1.5) and 38.50 diopter (refractive error: −0.75, uncorrected vision: 1.2), respectively, and more significant improvement was observed.

As above, the effect of the present invention has been apparently proved. Further, when the contact lenses prepared by the technique according to the present invention were worn by an astigmatic patient, a similar same effect to that in the case of myopia could be obtained The above results demonstrate the effect of the present invention.

What is claimed is:

1. A method for treating myopia of the right and left eyes of a patient, comprising:

measuring the topography of the right and left eyes of the patient;

providing a first contact lens pair, wherein each contact lens includes a pressure zone having a first surface with a curvature BC, a relief zone having a second surface with a curvature RC, a first anchor zone having a third surface with a curvature AC1, and a second anchor zone having a fourth surface with a curvature AC2;

determining said curvature BC according to the topography measurements;

determining said curvature RC, wherein said curvature RC equals said curvature BC plus 12.0;

determining said curvature AC1, wherein said curvature AC1 equals said curvature BC plus 5.0;

determining said curvature AC2, wherein said curvature AC2 equals said curvature BC plus 4.0;

fabricating said each contact lens of said first contact lens pair according to said curvature BC, said curvature RC, said curvature AC1 and said curvature AC2;

instructing the patient to wear said first contact lens pair for a first specified period of time;

providing a second contact lens pair, wherein each contact lens includes a pressure zone having a first surface with a curvature BC', a relief zone having a second surface with a curvature RC', a first anchor zone having a third surface with a curvature AC1', and a second anchor zone having a fourth surface with a curvature AC2';

determining said curvature BC' according to the topography measurement;

determining said curvature RC', wherein said curvature RC equals said curvature BC' plus 13.5;

determining said curvature AC1', wherein said curvature AC1' equals said curvature BC' plus 5.0;

determining said curvature AC2', wherein said curvature AC2' equals said curvature BC' plus 4.0;

fabricating said each contact lens of said second contact lens pair according to said curvature BC', said curvature RC', said curvature AC1' and said curvature AC2';

instructing the patient to wear said second contact lens pair for a second specified period of time.

2. A method according to claim 1, wherein said first specified period of time is about five weeks, and said second specified period of time is about five weeks.

3. A method according to claim 1, wherein said each contact lens of said first contact lens pair and said each contact lens of said second contact lens pair have diameters of about 10 millimeters.

4. A method according to claim 3, wherein said pressure zones of said first contact lens pair and said second contact lens pair have radiuses of about 6 millimeters, said relief zones of said first contact lens pair and said second contact lens pair have annular radiuses of about 0.7 millimeters, said first anchor zones of said first contact lens pair and said second contact lens pair have annular radiuses of about 0.7 millimeters and said second anchor zones of said first contact lens pair and said second contact lens pair have annular radiuses of about 0.7 millimeters.

5. A method according to claim 1, further comprising the steps of providing said each lens of said first contact lens pair and said each lens of said second contact lens pair with second relief zones, wherein said second relief zones have annular radiuses of about 0.4 millimeters.

6. A method according to claim 1, wherein said first contact lens pair and said second contact lens pair are selectively fabricated from fluroperm 60 and fluroperm 90.

* * * * *